United States Patent [19]
Koehn et al.

[11] Patent Number: 5,091,368
[45] Date of Patent: Feb. 25, 1992

[54] BIOLOGICALLY ACTIVE COMPOUNDS FROM BLUE-GREEN ALGAE

[75] Inventors: Frank Koehn; Sue S. Cross, both of Fort Pierce; Ross E. Longley, Vero Beach, all of Fla.

[73] Assignee: Harbor Branch Oceanographic Institution, Inc., Fort Pierce, Fla.

[21] Appl. No.: 564,817

[22] Filed: Aug. 8, 1990

[51] Int. Cl.$^5$ .................... C07K 5/10; A61K 37/02
[52] U.S. Cl. .................... 514/18; 530/317; 530/330
[58] Field of Search .................... 530/330, 317; 514/18

[56] References Cited

U.S. PATENT DOCUMENTS

| | | | |
|---|---|---|---|
| 4,342,751 | 8/1982 | Moore et al. | 530/317 |
| 4,548,814 | 10/1985 | Rinehart, Jr. | 424/95 |
| 4,729,996 | 3/1988 | Wright et al. | 514/215 |
| 4,737,510 | 4/1988 | Rinehart, Jr. | 514/388 |
| 4,808,590 | 2/1989 | Higa et al. | 514/272 |
| 4,921,873 | 5/1990 | Higa et al. | 514/546 |
| 4,970,226 | 11/1990 | Sun et al. | 514/397 |

OTHER PUBLICATIONS

Bolis, "Renin Inhibitors", J. Med. Chem. 30, 1729–1737, (1987).
Haber, "Renin Inhibitors", J. Cardiovascular Pharmacology 10 Suppl. 7 554–558 1987.
CA 112: 20472g "Isolation and Purification of Cytostatic Dolastatin", Pettit et al. (1990).
CA 110: 131823h, "Majusculamide D and Deoxymajusculamide D, Two Cytotoxin", Moore et al. (1989).
CA 112: 292c "Isolation and Structure of Cytostatic Linear Depsipeptide Dolastatin", Pettit et al. (1990).
Plattner, "Renin Inhib.", J. Med. Chem. 1988, 31, 2277–2288.
Faulkner, D. J. (1984) Natural Products Reports 1:551–598.
Faulkner, D. J. (1986) Natural Products Reports 3:1–33.
Faulkner, D. J. (1987) Natural Products Reports 4:539–576.
Uemura, D., K. Takahashi, T. Yamamoto, C. Katayama, J. Tanaka, Y. Okumura, and Y. Hirata (1985) "Norhalichondrin A: An Antitumor Polyether Macrolide from a Marine Sponge," J. Am. Chem. Soc. 107:4796–4798.
Castiello, D., G. Cimino, S. De Rosa, S. De Stefano, and G. Sodano (1980) "High Molecular Weight Polyacetylenes From the Nudibranch *Peltodoris atromaculata* and the Sponge *Petrosia ficiformis*," Tetrahedron Letters 21:5047–5050.
Moore, R. E., and M. Entzeroth (1988) "Majusculamide D and Deoxymajusculamidem D, Two Cytotoxins from *Lyngbya majuscula*," Phytochemistry 27(10:3101–3103.

Primary Examiner—Howard E. Schain
Assistant Examiner—L. Touzeau
Attorney, Agent, or Firm—Saliwanchik & Saliwanchik

[57] ABSTRACT

Novel bioactive compounds have been isolated from blue-green alga. These compounds have been found to have antitumor, antiviral, and immunomodulatory properties. Thus, these compounds, and derivatives thereof, can be used to treat human and animal tumors, inhibit viral growth, and provide immunomodulatory activity.

9 Claims, No Drawings

BIOLOGICALLY ACTIVE COMPOUNDS FROM BLUE-GREEN ALGAE

BACKGROUND OF THE INVENTION

Considerable research and resources have been devoted to oncology and antitumor measures including chemotherapy. Tumors inflict mammals and man with a variety of disorders and conditions including various forms of cancer and resultant cancerous cachexia, which term refers to the symptomatic discomfort that accompanies the infliction of a mammal with a tumor. Such symptoms include weakened condition of the inflicted mammal as evidenced by weight loss, etc. The seriousness of cancer is well known since cancer is a major cause of death in man. While certain methods and chemical compositions have been developed which aid in inhibiting, remitting, or controlling the growth of tumors new methods and antitumor chemical compositions are needed.

Viral diseases also inflict man, plants, insects and animals. The prevention and control of viral diseases has important health and economic implications. Viral diseases contribute to inflictions in humans including the common cold, herpes, acquired immune deficiency syndrome (AIDS), and cancer, so the importance of their control is obvious. Also important is the control of viral diseases in animals for economic and other reasons, e.g., the ability of such animals to become virus reservoirs or carriers which facilitate the spreading of viral diseases to humans. Viral plant diseases have been known to have a disruptive effect on the cultivation of fruit trees, tobacco, and various vegetables. Insect viral diseases are also of interest because of the insects' ability to transfer viral diseases to humans.

The prevention and control of viral diseases is thus of prime importance to man, and considerable research has been devoted to antiviral measures. Certain methods and chemical compositions have been developed which aid in inhibiting, controlling, or destroying viruses, but additional methods and antiviral compositions are needed.

It has been found that some natural products and organisms are potential sources for chemical molecules having useful biological activity of great diversity. Marine life has been the source for the discovery of compounds having varied biological activities. Some of the United States patents which have issued for such inventions are as follows: U.S. Pat. No. 4,548,814 for didemnins, having antiviral activity, were isolated from a marine tunicate; U.S. Pat. No. 4,729,996 discloses compounds, having antitumor properties, that were isolated from marine sponges *Teichaxinella morchella* and *Ptilocaulis walpersi*; U.S. Pat. No. 4,80,590 discloses compounds, having antiviral, antitumor, and antifungal properties, isolated from the marine sponge *Theonella sp.*; and U.S. Pat. No. 4,737,510 discloses compounds, having antiviral and antibacterial properties, isolated from the Caribbean sponge *Agleas coniferin*. Clearly, marine sponges have proved to be a source of biological compounds, and a number of publications have issued disclosing organic compounds derived from marine sponges, including Scheuer, P. J. (ed.) *Marine Natural Products, Chemical and Biological Perspectives*, Academic Press, New York, 1978-1983, Vol I-V; Faulkner, D. J., (1984) Natural Products Reports 1:551-598; Natural Products Reports (1986) 3:1-33; Natural Products Reports (1987) 4:539-576; Natural Products Report (1988) 5:613-663; J. Am. Chem. Soc. (1985) 107:4796-4798.

In addition to marine sponges, many other types of marine organisms have been investigated for biologically active compounds. The following publications also describe compounds obtained from marine organisms:

Castiello, D., G. Cimino, S. De Rosa, B. De Stefano, and G. Sodano (1980) "High molecular weight polyacetylenes from the nudibranch *Peltodoris atromaculata* and the sponge *Petrosia ficiformis*," Tetrahedron Letters 21:5047-5050;

U.S. Pat. No. 4,548,814 for didemnins from a marine tunicate; and

Moore, R. E., and M. Entzeroth (1988) "Majusculamide D and deoxymajusculamide D, two cytotoxins from *Byngbya majuscula*," Phytochemistry 27(10):3101-3103.

BRIEF SUMMARY OF THE INVENTION

The subject invention pertains to novel biologically active peptides from blue-green algae. These compounds are known as microcolin A and microcolin B. The microcolins and their analogs have antiviral, cytotoxic, and immunomodulatory properties. Pharmaceutical compositions comprising these compounds could be used in the treatment of viral, immunological, or cancer related diseases in humans or animals.

The structures of the microcolins are shown below:

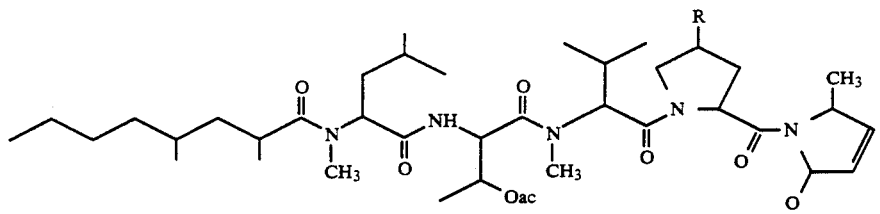

R = OH(Microcolin A)

R = H(Microcolin B)

DETAILED DESCRIPTION OF THE INVENTION

The subject invention pertains to novel compounds isolated from blue-green algae. These compounds have been shown to possess antiviral, cytotoxic, and immunomodulatory properties. The subject invention pertains to the compounds themselves, as well as pharmaceutical compositions containing these compounds. Also disclosed and claimed are methods for administering the novel compositions. Various derivatives of these compounds can be produced by known procedures. The compounds of interest can be isolated from blue-green algae as described below.

Blue-green alga was collected by scuba from 40-90' on a fore reef slope at Pta. Bobos, La Blanquilla, Venezuela (11° 49.40′ N, 64° 38.63′ W). A taxonomic sample voucher specimen has been deposited in the HHBIO/IRCZM Herbarium accession number HBFH 6205. The sample has been identified as *Lyngbya plectonema permidium* LPP group A, or *Microcoleus lyngbyaceus* (see Humm, H. J. and S. R. Wicks. 1980. *Introduction and Guide to the Marine Blue-green Algae.* John Wiley and Sons, New York p. 194).

Isolation and Identification of Microcolins A & B

Frozen *M. lyngbyaceus* (146 gram wet weight) was lyophilized overnight to give 60.9 grams dry organism. The dry material was homogenized with 100% ethanol in a Waring blender, allowed to stand for 30 minutes, and filtered. This procedure was repeated on the remaining solids and the resulting extracts were combined and evaporated under reduced pressure to give 3.54 grams of extract (crude). The crude material wa partitioned between $CH_2Cl_2$:methanol:$H_2O$(3:2:1) to give 620 mg and 2.68 grams of nonpolar and polar fractions, respectively. The nonpolar material was dissolved in 10 ml EtOAc, mixed with 3 grams of silica gel (Merck 60) and loaded onto a column of 30 grams of silica gel. The column was eluted (VLC) stepwise with EtOAc/hexane mixtures of increasing polarity up to 100% EtOAc. Active fractions were combined, evaporated, and loaded into a column of 5 grams $C_{18}$ silica gel (Amicon) and eluted (VLC) with 75% acetonitrile:water to remove residual pigments. The eluted fraction was evaporated and chromatographed by HPLC (reversed phase $C_{18}$ Vydac, 10 micron, 70-75% acetonitrile/water) to give 10.6 gm of microcolin A and 6.3 mg of microcolin B. The structures of microcolins A and B were elucidated by mass spectrometry, chemical analysis, and one- and two-dimensional NMR spectroscopy. Following are the spectral data from the microcolin compounds.

TABLE 1

Microcolin A. $^1$H NMR, $CDCl_3$, 360 MHz

δ

7.23, 1H, dd, J = 6.1, 2.0
6.99, 1H, d, J = 8.9
6.05, 1H, dd, J = 6.1, 1.7
5.62, 1H, dd, J = 7.7, 2.2
5.24, 1H, dd, J = 10.2, 5.6
5.22, 1H, dd, J = 6.5, 2.9
4.98, 1H, d, J = 11.1
4.92, 1H, dd, J = 8.9, 2.9
4.79, 1H, qt, J = 6.7, 1.7
4.34, 1H, bm
3.80, 2H, m
3.06, 3H, s
2.93, 3H, s
2.80, 1H, m
2.45, 1H, ddd
2.21, 1H, ddd
1.98, 3H, s
1.84, 1H, ddd
1.70, 1H, ddd
1.54, 1H, ddd
1.43, 3H, d, J = 6.7
1.37, 1H, m
1.23, 8H, bm
1.12, 3H, d, J = 6.5
1.09, 3H, d, J = 6.8
1.05, 1H, m
0.95, 3H, d, J = 6.5

TABLE 1-continued

Microcolin A. $^1$H NMR, $CDCl_3$, 360 MHz

δ

0.91, 3H, d, J = 6.6
0.85, 3H, t, J = 6.6
0.83, 3H, d, J = 6.7
0.82, 3H, d, J = 6.6
0.78, 3H, d, J = 6.6

TABLE 2

Microcolin A. $^{13}$C NMR, $CDCl_3$, 90 MHz

| δ | (m) |
|---|---|
| 177.9 | s |
| 174.6 | s |
| 171.3 | s |
| 169.8 | s |
| 169.8 | s |
| 169.7 | s |
| 168.9 | s |
| 154.1 | s |
| 125.3 | d |
| 71.8 | d |
| 68.4 | d |
| 59.2 | d |
| 58.6 | d |
| 58.1 | d |
| 56.9 | d |
| 53.7 | d |
| 51.8 | d |
| 41.9 | t |
| 37.1 | t |
| 36.6 | t |
| 35.8 | t |
| 33.8 | d |
| 30.7 | q |
| 30.3 | q |
| 30.3 | d |
| 29.1 | t |
| 27.1 | d |
| 24.8 | d |
| 23.3 | q |
| 22.9 | t |
| 21.5 | q |
| 21.0 | q |
| 19.5 | q |
| 18.8 | q |
| 18.4 | q |
| 18.2 | q |
| 17.4 | q |
| 16.9 | q |
| 14.1 | q |

TABLE 3

Microcolin B. $CDCl_3$, $^1$H NMR, 360 MHz

| δ | (m, J) |
|---|---|
| 7.22, | 1H, dd, J = 6.0, 1.9 |
| 6.95, | 1H, d, J = 9.2 |
| 6.03, | 1H, dd, J = 6.0, 1.7 |
| 5.45, | 1H, dd, J = 8.4, 5.2 |
| 5.25, | 1H, dd, J = 6.0, 10 |
| 5.24, | 1H, dd, J = 7.0, 2 |
| 5.02, | 1H, d, J = 11.0 |
| 4.95, | 1H, dd, J = 8.9, 3.7 |
| 4.74, | 1H, qt, J = 6.9, 1.7 |
| 3.74, | 2H, dm |
| 3.15, | 3H, s |
| 2.91, | 3H, s |
| 2.82, | 1H, m |
| 2.40, | 1H, m |
| 2.25, | 1H, m |
| 1.97, | 3H, s |
| 2.0, | 1H, m |
| 1.93, | 1H, m |
| 1.85, | 1H, m |
| 1.80, | 1H, m |
| 1.70, | 1H, m |
| 1.56, | 1H, m |

TABLE 3-continued

Microcolin B. CDCl₃. ¹H NMR, 360 MHz

| δ | (m, J) |
|---|---|
| 1.44, | 3H, d, J = 6.8 |
| 1.40, | 1H, m |
| 1.30, | 1H, m |
| 1.30, | 6H, bm |
| 1.13, | 3H, d, J = 6.5 |
| 1.11, | 3H, d, J = 6.8 |
| 1.10, | 1H, m |
| 0.97, | 3H, d, J = 6.5 |
| 0.92, | 3H, d, J = 6.5 |
| 0.86, | 3H, t, J = 6.5 |
| 0.84, | 3H, d, J = 6.5 |
| 0.82, | 3H, d, J = 6.5 |
| 0.78, | 3H, d, J = 6.5 |

TABLE 4

¹³C NMR Microcolin B CDCl₃, 90 MHz

| # | δ | m |
|---|---|---|
| 1 | 177.9 | s |
| 2 | 172.0 | s |
| 3 | 171.3 | s |
| 4 | 169.7 | s |
| 5 | 169.7 | s |
| 6 | 169.8 | s |
| 7 | 168.3 | s |
| 8 | 153.7 | d |
| 9 | 125.5 | d |
| 10 | 68.9 | d |
| 11 | 60.0 | d |
| 12 | 59.3 | d |
| 13 | 58.0 | d |
| 14 | 53.8 | d |
| 15 | 52.0 | d |
| 16 | 48.0 | t |
| 17 | 41.9 | t |
| 18 | 37.0 | t |
| 19 | 35.9 | t |
| 20 | 33.8 | d |
| 21 | 30.8 | d |
| 22 | 30.5 | q |
| 23 | 30.4 | q |
| 24 | 29.1 | t |
| 25 | 28.9 | t |
| 26 | 27.3 | d |
| 27 | 24.9 | d |
| 28 | 24.6 | t |
| 29 | 23.3 | q |
| 30 | 22.9 | t |
| 31 | 21.6 | q |
| 32 | 21.0 | q |
| 33 | 19.6 | q |
| 34 | 18.9 | q |
| 35 | 18.4 | q |
| 36 | 18.2 | q |
| 37 | 17.2 | q |
| 38 | 17.2 | q |
| 39 | 14.1 | q |

For microcolin B the following information was also obtained:
HREIMS - meas. m/z 731.4797
calc. for $C_{39}H_{65}O_8N_5$
Δ2.4 mmu.
Optical rotation $[\alpha]_D^{23} = -174°$ (C=0.005 ethanol).

Biological Assays for the Microcolins

The microcolins were assayed to determine their immunomodulatory, antiviral, and cytotoxic properties. The assays conducted are described below.

I. Mixed Lymphocyte Reaction

1. Murine splenocyte suspensions were prepared separately from BALB/c and C57BL/6J mice. Spleens were aseptically removed and homogenized in RPMI-1640 tissue culture medium (TCM), supplemented with 10% fetal calf serum, 2% 1-glutamine, 15 mM HEPES, 1% antibiotic-antimycotic solution, and 25 μg/ml gentamicin (GIBCO). The cell concentrations were adjusted to $2.5 \times 10^6$ cells/ml. Aliquots of each cell population were removed to separate tubes, and the remaining two cell suspensions combined to one tube.

2. Serial, log₁₀ dilutions of the crude extract, or serial two-fold dilutions of the pure compound were made in absolute ethanol, and 10 μl of each dilution was added to wells of microtiter test plates, and allowed to dry.

3. A volume of 0.2 ml of the combined splenocyte suspensions was added to triplicate test wells. Positive control wells received combined splenocyte suspensions in the absence of the test extracts/compounds. Negative control wells consisted of separate (not mixed) splenocyte suspensions cultured in the absence of the test compounds.

4. Plates were incubated in 5% $CO_2$ at 37° C. for 86 hours.

5. A volume of 0.05 ml of ³H-thymidine (20 μCk/ml) was added to each well, and the plates were incubated in 5% $CO_2$ at 37° C. for an additional 5 hours.

6. The contents of each well of the microtiter plates were harvested onto glass fiber filter strips, and the resulting filter discs placed in scintillation vials to which 2.0 ml of scintillation fluid was added.

7. The amount of incorporated ³H-thymidine was determined by counting the vials in a liquid scintillation counter.

8. Triplicate counts were averaged, and the data reported as a percentage of the positive control. A value of less than 10% of the positive control MLR with a corresponding LCV value of >70% suggest optimal immunosuppressive effects of the extract/compound.

II. Lymphocyte Viability Assay

1. Extra and compounds were similarly tested in parallel with the MLR to determine their toxic effects on lymphoid cells using the lymphocyte viability assay (LCV).

2. Serial, log₁₀ dilutions of the crude extract or serial two-fold dilutions of the pure compound were made in absolute ethanol, and 10 μl of each dilution was added to wells of microtiter test plates, and allowed to dry.

3. Murine splenocyte suspensions were prepared from BALB/c mice. Spleens were aseptically removed and homogenized in RPMI-1640 tissue culture medium (TCM), supplemented with 10% fetal calf serum, 2% 1-glutamine, 15 mM HEPES, 1% antibiotic-antimycotic solution, and 25 μg/ml gentamicin (GIBCO). The cell concentrations were adjusted to $2.5 \times 10^6$ cells/ml.

4. A volume of 0.2 ml of the splenocyte suspension was added to replicate test wells. Positive control wells received splenocyte suspensions in the absence of the test extracts/compounds.

5. Plates were incubated at 37° C. for 86 hours. At the end of the incubation period, a volume of 75 μl of a 2.0 mg/ml solution of MTT was added to each well, and the plates were returned to the incubator for an additional 5 hours.

6. The supernatants from each microwell were then removed, and a volume of 200 μl of isopropanol was added and the contents mixed.

7. Values were obtained by comparing the optical densities (determined at 570 and 650 nm) of wells containing the test compounds with those of wells containing cells and medium only (positive control). The results are expressed as a percentage of the positive control.

8. Replicate counts were averaged, and the data reported as a percentage of the positive control. An LCV value of less than 60% of the positive control is an indication of cytotoxicity of the test extracts/compounds for lymphoid cells.

Antiviral Assay

The antiviral assay for herpes simplex virus type 1 (HSV-1) is a plaque inhibition assay. CV-1 cells (a fibroblast-like cell culture derived from primary African green monkey cells) are infected with the Kos strain of HSV-1. Cytopathic effects (CPE) of the virus are prevented from rapid spread by a methylcellulose medium. Distinct areas of infected cells or plaques are distinguished from a surrounding area of viable CV-1 cells by staining the culture with neutral red which is a stain taken up by living cells. The viral dose can be quantitated by counting the number of plaques. Compounds with antiviral activity can be identified by comparing the plaque number in the drug treated cells to the HSV-1 viral control.

Assay Protocol

1. Cells - CV-1
2. Virus - Kos strain
3. Media

Growth Medium

Eagle's minimum essential medium in Earle's balanced salt solution (EMEM)
10% fetal bovine serum
1% nonessential amino acids (NEAA)
2 1-glutamine (200 mM)
1% sodium pyruvate
50 μg/ml gentamicin

Maintenance medium

First overlay: Equal volumes of a 2% solution of 4000 centipoise methylcellulose in distilled water and a 2× growth medium with 5% fetal bovine serum and without phenol red. Second overlay: Equal volumes of a 4% solution of 15 centipoise methylcellulose in distilled water and a 2× growth medium with 5% fetal bovine serum without phenol red containing 0.1 mg/ml neutral red dye for the 1× solution.

Trypsin solution 0.5 mg/ml trypsin and 0.2 mg/ml EDTA•4Na in Dulbecco's phosphate buffered saline without $CaCl_2$ and $MgCl_2 \cdot 6H_2O$ (PBS).

4. Growth of CV-1 cells

Confluent cultures of CV-1 cells are rinsed with PBS two times and 4.0 ml trypsin solution is added to 150 $cm^2$ tissue sulture flask. Cells are dispersed an $10 \times 10^6$ CV-1 cells in 40 ml of growth medium are added to new 150 $cm^2$ flasks. The number of cells added to a cell culture flask is proportional to the area. The cell culture is confluent in 5 to 7 days for use in the antiviral assay.

5. Antiviral assay

Twenty-four well plates (16 mm diameter per well) are seeded with $2 \times 10^5$ cells per well in 0.5 ml growth medium and incubated at 37°) C. with 5% $CO_2$. The plates are used in 24 to 72 hours. Each well is infected with at least 25 but no more than 80 plaque forming units (PFU) of virus. Plates are incubated for 1.0 hours at 37° C. with 0.2 ml virus. At the end of the incubation period, the fluid containing the viral inoculum is removed from the plates and 0.5 ml of the first overlay medium is added.

For antiviral tests of extracts and pure compounds, samples are added to filter paper discs (6 mm diameter) and solvents are allowed to evaporate.

Discs are placed in wells containing cells, virus, and overlay medium. Plates are incubated at 37° C. for 48 hours, the second overlay medium is added at 0.5% ml per well, and, after 24 hours additional incubation time, the plates are read.

Antiviral activity

Antiviral activity is observed from two parameters. One is actual reduction in the number of plaques and the second is the diminution in plaque diameter.

Drug cytotoxicity

Wells of plates are 16 mm in diameter and discs are 6 mm in diameter.

Zones of cytotoxicity greater than 6 mm are graded from 8 to 16 using only even numbers.

0 = no macroscopic or microscopic toxicity
16 = 100% cell destruction 8, 10, 12, 14 = diameter of toxic zone including diameter of 6 mm disc.

Antiviral activity

+++ = complete inhibition of plaque formation
++ = partial inhibition
+ = partial inhibition
+/− = marginal inhibition
− = no protection The fifty per cent minimum inhibitory concentration ($MIC_{50}$) is determined by counting the number of plaques in the experimental drug tests and comparing the values to the viral control wells or by estimating the plaque reduction values from the inhibition values with +++ = 100 reduction, ++ = 75%, + 50%, +/− =25%, and − = no reduction in plaque number compared to controls.

Antitumor Methodology

The crude extract and pure compound was tested for toxicity against murine P388 leukemia cells. P388 cells obtained from J. Mayo, National Cancer Institute, Bethesda, Md., were maintained in Roswell Park Memorial Institute medium 1640 (RPMI-1640) supplemented with 10% horse serum. All cell lines were cultured in plastic tissue culture flasks and kept in an incubator at 37° C. in humidified air containing 5% $CO_2$. Antibiotic-free stock cultures of P388 cells were subcultured to $10^5$ cells/ml by dilution in fresh growth medium at 2-3 day intervals. The means generation time of primary cultures was 14–17 hours.

To assess the antiproliferative effects of agents against P388 cells, 200 μl cultures (96-well tissue culture plates, Nunc, Denmark) were established at $1 \times 10^6$ cells/ml in drug-free medium or medium containing the crude extract at a final dilution of 1:500 of compound 1 or 2 at various concentrations. Solvent for all dilutions was methanol, which was removed from plates under vacuum. All experimental cultures were initiated in medium containing Gentamicin sulfate (50 mg/ml; Schering Corporation, Kenilworth, N.J.). After 48 hour exposures, P388 cells were enumerated using 3-[4,5- dimentylthiazol-2-yl]-2,5-diphenyltetrazolium bromide (MTT) as described below (Alley, M. C. et al.[1988]-Cancer Res. 48:589).

To quantitate the effects on cell proliferation, 75 μl of warm growth medium containing 5 mg/ml MTT was added to each well and cultures were returned to the incubator for 90 minutes. To spectophotometrically quantitate formation of reduced formazan, plates were centrifuged (900 xg, 5 minutes), culture fluids removed by aspiration, and 200 μl of acidified isopropanol (2 ml concentrated HCl/liter isopropanol) added per well. The absorbance of the resulting solutions were measured at 570 nm with a plate reader (MR700 Microplate Reader, Dynatech Laboratories, Chantilly, Va.). The absorbance of test wells was divided by the absorbance of drug-free wells, and the concentration of agent that resulted in 50% of the absorbance of untreated cultures was determined by linear regression of logit-transformed data (Finney, D. J. *Statistical Method in Biological Assay*, 3rd Ed., pp. 316-348, Charles Griffin Co., London, 1978). A linear relationship between P388 cell number and formazan production was found over the range of cell densities observed in these experiments.

Following are examples which illustrate procedures, including the best mode, for practicing the invention. These examples should not be construed as limiting. All percentages are by weight and all solvent mixture proportions are by volume unless otherwise noted.

EXAMPLE 1

Antitumor Activity of Crude Extract

Toxicity of the crude extract against murine P388 leukemia cells was assayed as described above. It was found that the crude extract had an $IC_{50}$ of 0.35 μg/ml. At a concentration of 20 μg/ml, 98% inhibition was observed.

EXAMPLE 2

Antiviral Activity of Crude Extract

The antiviral activity of the crude extract against several types of viruses was assayed as described above. The results of these assays are shown in Table 5 below.

TABLE 5

| | Antiviral activity of crude extract | | |
|---|---|---|---|
| Virus | No diultion | 10-fold dilution | 100-fold dilution |
| HSV-1 | 0++/+ | 0++ | 0+ |

EXAMPLE 3

Immunomodulatory Ability of Crude Extract

The crude extract was assayed for immunomodulatory and cytotoxic activity as described above. The results of these assays are shown in Table 6, below.

TABLE 6

| Immunomodulatory and cytotoxic activity of the crude extract | | | |
|---|---|---|---|
| Conc. (dilution) | [1]% MLR Control | [2]% LCV Control | |
| 0.0 (control) | <1 | 8 | [3]ID/Cytotoxic |
| 0.1 | <1 | 26 | ID/Cytotoxic |
| 0.01 | <1 | 56 | ID/Cytotoxic |

TABLE 6-continued

| Immunomodulatory and cytotoxic activity of the crude extract | | |
|---|---|---|
| Conc. (dilution) | [1]% MLR Control | [2]% LCV Control |
| 0.001 | 142 | 119 |

[1]Percent of the positive control (no drug) MLR response.
[2]Percent of the positive control (no drug) LCV response.
[3]ID/Cytotoxic = immunosuppressive but with associated cytotoxicity (LCV values <70% of the positive control (no drug)).

EXAMPLE 4

Antiviral Activity of Pure Compounds

Pure microcolin A and microcolin B were assayed for their activity against HSV-1. The results of these assays are shown in Table 7, below.

TABLE 7

| Anti-HSV-1 activity of microcolins A and B | | | |
|---|---|---|---|
| | $ID_{50}$ (nanograms/ml) | $ED_{50}$ (nanograms/ml) | TI |
| Microcolin A | 480 | 2.5 | 192 |
| Micorcolin B | 1185 | 146.0 | 8 |

EXAMPLE 5

Immunomodulatory Activity of Pure Compounds

The immunomodulatory activity of pure microcolin A and microcolin B were assayed as described above. The results of these assays are shown below in Tables 8 and 9.

TABLE 8

| Immunomodulatory activity of microcolin A. | | | |
|---|---|---|---|
| Conc. (ng/ml) Microcolin A | [1]% MLR Control | [2]% LCV Control | |
| 0.0 (control) | 100 | 100 | |
| 2.5 | <1 | 78 | [3]ID |
| 5.0 | <1 | 71 | ID |
| 10.0 | <1 | 80 | ID |
| 20.0 | <1 | 82 | ID |
| 40.0 | <1 | 60 | |
| 80.0 | <1 | 59 | |
| 160.0 | <1 | 59 | |
| 312.5 | <1 | 48 | |
| 625.0 | <1 | 52 | |
| 1250.0 | <1 | 31 | |
| 2500.0 | <1 | 18 | |
| 5000.0 | <1 | 3 | |

[1]Percent of the positive control (no drug) MLR response.
[2]Percent of the positive control (no drug) LCV response.
[3]ID = immunosuppressive (corresponding LCV values must be 70% of control (no drug) or greater).

TABLE 9

| Immunomodulatory activity of Microcolin B. | | | |
|---|---|---|---|
| Conc. (ng/ml) Microcolin A | [1]% MLR Control | [2]% LCV Control | |
| 0.0 (control) | 100 | 100 | |
| 2.5 | 93 | 78 | |
| 5.0 | 87 | 121 | |
| 10.0 | 80 | 107 | |
| 20.0 | 39 | 105 | [3]ID |
| 40.0 | 1 | 97 | ID |
| 80.0 | <1 | 114 | ID |
| 160.0 | <1 | 99 | ID |
| 312.5 | <1 | 110 | ID |
| 625.0 | <1 | 88 | ID |
| 1250.0 | <1 | 75 | ID |
| 2500.0 | <1 | 51 | |

TABLE 9-continued

| Immunomodulatory activity of Microcolin B. | | |
|---|---|---|
| Conc. (ng/ml) Microcolin A | [1]% MLR Control | [2]% LCV Control |
| 5000.0 | <1 | 29 |

[1] Percent of the positive control (no drug) MLR response.
[2] Percent of the positive control (no drug) LCV response.
[3] ID = immunosuppressive (corresponding LCV values must be 70% of control (no drug) or greater).

EXAMPLE 6

Antitumor Activity of Pure Compounds

Pure microcolin A and B were assayed for toxicity against murine P388 leukemia cells as described above. The $IC_{50}$ of mirocolin A was found to be 0.0009 μg/ml while microcolin B was found to have an $IC_{50}$ of 0.096 μg/ml.

EXAMPLE 7

Analogs of Structure

Various derivatives and analogs of these compounds can be produced by known procedures. Examples of derivatives and analogs are shown below.

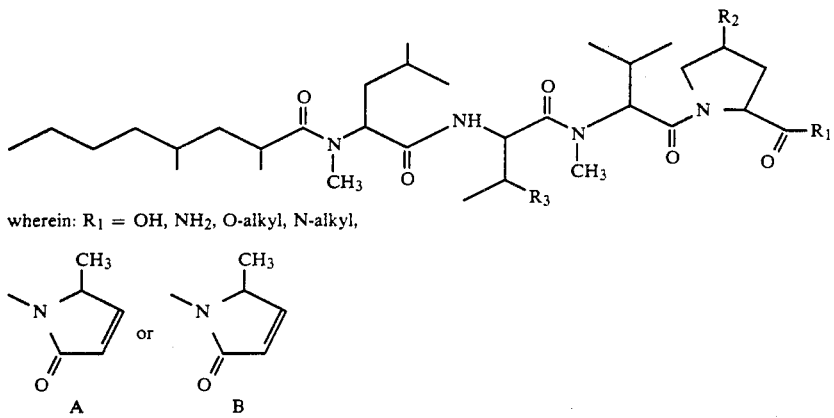

wherein: $R_1$ = OH, $NH_2$, O-alkyl, N-alkyl, $R_2$ = H, OH, =O, O-alkyl, O-acyl, =N-HOH, =NNHR, =NNHCONH$_2$, or =NO-alkyl;
$R_3$ = OH, =O, O-alkyl, =NNHR, =NNHCONH$_2$, O-acyl, =NOH, or =NO-alkyl; R=aryl or alkyl.

A number of useful analogs of microcolin A and B can be prepared. Compounds with modified $R_1$ and $R_2$ groups can be prepared by cleavage of either microcolin A or B in mildly basic alcohol. These compounds can be further derivatized by reacting with appropriate alcohols (methanol, ethanol, propanol, etc.) or equivalent amines under suitable conditions to yield esters where $R_1$ is O-alkyl or amides where $R_1$ is $NH_2$ or N-alkyl. The parent or modified compounds can be reacted with various acyl chlorides to yield derivatives where $R_2$ is O-acyl. Compounds where $R_2$ is =O can be prepared from microcolin A, or derivatives thereof as described above, using one of a number of oxidation procedures known to those skilled in the art. These include, but are not limited to, reaction with acetic anhydride, dimethylsulfoxide, and acid catalysis, i.e., the Moffat procedure, or reaction with pyridinium dichromate in organic solvents. The resulting ketone derivatives of microcolin A are then used to furnish oxime derivatives where $R_2$ is =NOH or =NO-alkyl by reaction with appropriately substituted hydroxylamines. Other carbonyl derivatives such as hydrazones and semicarbazones can be prepared by reaction with appropriately substituted hydrazines or semicarbizides.

Compounds where $R_1$ =B can be prepared from either microcolin A or B by reaction with high pressure hydrogen gas in an appropriate solvent such as ethanol in the presence of a catalyst such as platinum or palladium-on-carbon. Other metal catalysts could be used as well. Compounds where $R_3$ is OH or O-acyl can be prepared from those described above by solvolysis followed by reaction with various acyl chlorides.

EXAMPLE 8

Formulation and Administration

The compounds of the invention are useful for various non-therapeutic and therapeutic purposes. It is apparent from the testing that the compounds of the invention are effective for immunomodulation, antiviral activity, and for controlling tumor growth. The compounds can be used to inhibit unwanted viral growth in the work areas of virology labs. Also, the compounds can be used as ultraviolet screeners in the plastic industry since they effectively absorb UV rays. As disclosed herein, they can be used therapeutically for treating tumors, or as immunomodulatory or antiviral agents in animals and humans.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the infection, the type of host involved, its age, weight, health, kind of concurrent treatment, if any, frequency of treatment, and therapeutic ratio.

The compounds of the subject invention can be formulated according to known methods for preparing pharmaceutically useful composition. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

Examples of such carrier for use in the invention include ethanol, dimethyl sulfoxide, glycerol, silica, alumina, starch, and equivalent carrier and diluents. While effective amounts may vary, as conditions in which such compositions are used vary, a minimal dosage required for antiviral activity is generally between 50 and 200 micrograms against 25–80 plaque-forming units of virus. To provide for the administration of such dosages for the desired therapeutic treatment, new pharmaceutical compositions of the invention will advantageously comprise between about 0.1% and 45%, and especially, 1 and 15%, by weight of the total composition including carrier or diluent. Illustratively, dosage levels of the administered active ingredients can be: intravenous, 0.01 to about 20 mg/kh; intraperitoneal, 0.01 to about 100 mg/kh; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The compounds of the subject invention can be parenterally, orally, or topically administered to subjects requiring antiviral or antitumor treatment. The active compounds may be mixed with physiologically acceptable fluids such as saline or balanced salt solutions. Also, solid formulations such as tablets or capsules can be made.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A compound having the following structure:

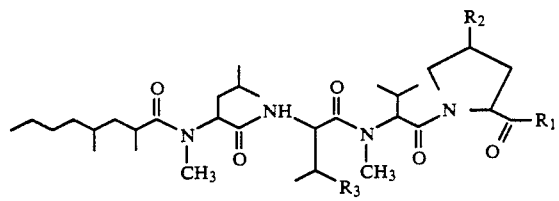

wherein: $R_1 = OH, NH_2, O\text{-alkyl}, N\text{-alkyl},$

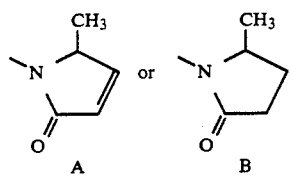

$R_2 = H, OH, =O, O\text{-alkyl}, O\text{-acyl}, =NHOH, =NNH\text{-}CONH_2, =NNHR, or =NO\text{-alkyl};$ $R_3 = OH, =O, O\text{-alkyl}, =NOH, or =NO\text{-alkyl};$ and $R = $ aryl or alkyl.

2. The compound, according to claim 1, wherein $R_1$ is A, $R_2$ is H, and $R_3$ is OAc.

3. The compound, according to claim 1, wherein $R_1$ is A, $R_2$ is OH, and $R_3$ is OAc.

4. A process for treating a human or animal hosting tumor cells, said process comprising administering to said human or animal an effective tumor cell-inhibiting amount of a compound having the following structure:

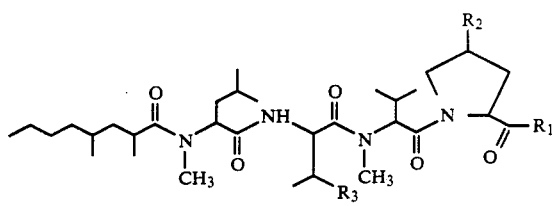

wherein: $R_1 = OH, NH_2, O\text{-alkyl}, N\text{-alkyl},$

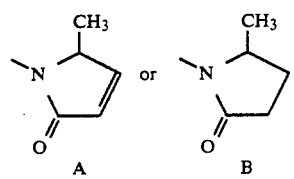

$R_2 = H, OH, =O, O\text{-alkyl}, O\text{-acyl}, =NHOH, =NNH\text{-}CNOH_2, =NNHR, or =NO\text{-alkyl};$ $R_3 = OH, =O, O\text{-acyl}, O\text{-alkyl}, =NOH, or =NO\text{-alkyl};$ and $R = $ aryl or alkyl.

5. The process, according to claim 4, wherein for said compound, $R_1$ is A, $R_2$ is H, and $R_3$ is OAc.

6. The process, according to claim 4, wherein for said compound, $R_1$ is A, $R_2$ is OH, and $R_3$ is OAc.

7. A process for treating a human or animal in need of immunomodulation, said process comprising administering to said animal an effective immunomodulatory amount of a compound having the following structure:

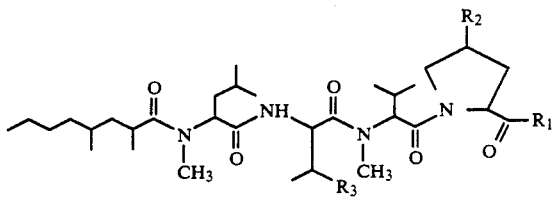

wherein: $R_1 = OH, NH_2, O\text{-alkyl}, N\text{-alkyl},$

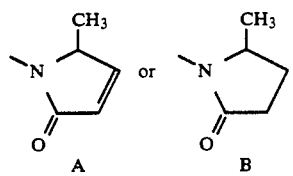

$R_2 = H, OH, =O, O\text{-alkyl}, O\text{-acyl}, =NHOH, =NNH\text{-}CONH_2, =NNHR, or =NO\text{-alkyl};$ $R_3 = OH, =O, O\text{-acyl}, O\text{-alkyl}, =NOH, or =NO\text{-alkyl};$ and $R = $ aryl or alkyl.

8. The process, according to claim 7, wherein for said compound, $R_1$ is A, $R_2$ is H, and $R_3$ is OAc.

9. The process, according to claim 7, wherein for said compound, $R_1$ is A, $R_2$ is OH, and $R_3$ is OAc.

* * * * *

UNITED STATES PATENT AND TRADEMARK OFFICE
CERTIFICATE OF CORRECTION

PATENT NO. : 5,091,368

DATED : February 25, 1992

INVENTOR(S) : Frank Koehn, Sue S. Cross, Ross E. Longley

It is certified that error appears in the above-identified patent and that said Letters Patent is hereby corrected as shown below:

Column 1: line 19: "tumors new" should read --tumors, new--; line 67: "4,80,590" should read --4,808,590--.

Column 2: line 4: "Agleas coniferin" should read --*Agelas coniferin*--; line 30: "*Byngbya*" should read --*Lyngbya*--; line 43:

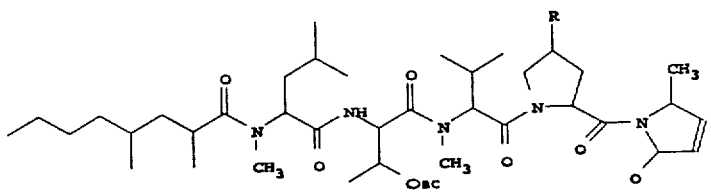

should read

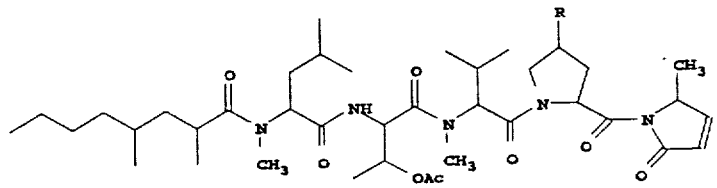

Column 3: line 7: "HHBIO/IRCZM" should read --HHBOI/IRCZM--; line 23: "material wa" should read --material was--.

UNITED STATES PATENT AND TRADEMARK OFFICE
CERTIFICATE OF CORRECTION

PATENT NO. : 5,091,368

DATED : February 25, 1992

INVENTOR(S) : Frank Koehn, Sue S. Cross, Ross E. Longley

It is certified that error appears in the above-identified patent and that said Letters Patent is hereby corrected as shown below:

Column 6: line 22: "(20μCK/ml)" should read --(20μCi/ml)--; line 39: "Extra and compounds" should read --Extracts and compounds--.

Column 7: line 36: "2 1 glutamine" should read --2% 1-glutamine--; line 58: "tissue sulture" should read --tissue culture--; line 68: "37°)C" should read --37°C--.

Column 8: line 56: "means generation" should read --mean generation--.

Column 10: line 58: "Microcolin A" should read --Microcolin B--.

Column 11: line 5: "Microcolin A" should read --Microcolin B--.

Column 11: Structure B:

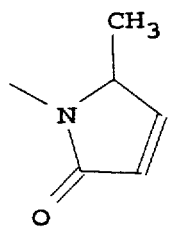 should read 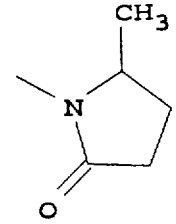

B                      B

Column 12: line 21: "plastic" should read --plastics--; line 61: "composition" should read --compositions--.

UNITED STATES PATENT AND TRADEMARK OFFICE
CERTIFICATE OF CORRECTION

PATENT NO.    :    5,091,368

DATED         :    February 25, 1992

INVENTOR(S)   :    Frank Koehn, Sue S. Cross, Ross E. Longley

It is certified that error appears in the above-identified patent and that said Letters Patent is hereby corrected as shown below:

Column 13:  line 4: "carrier" should read --carriers--; line 15: "by weight of the total composition including carrier or diluent" should read --by weight of the total of one or more of the new compounds based on the weight of the total composition including carrier or diluent--; line 18: "20 mg/kh" should read --20 mg/kg--; line 19: "100 mg/kh" should read --100 mg/kg--.

Signed and Sealed this

Sixth Day of July, 1993

Attest:

MICHAEL K. KIRK

*Attesting Officer*    *Acting Commissioner of Patents and Trademarks*